United States Patent [19]

Azuara

[11] Patent Number: 5,576,326
[45] Date of Patent: *Nov. 19, 1996

[54] COPPER AMINO ACIDATE DIIMINE NITRATE COMPOUNDS AND THEIR METHYL DERIVATIVES AND A PROCESS FOR PREPARING THEM

[75] Inventor: Lena R. Azuara, Villa de Cortes, Mexico

[73] Assignee: Universidad Nacional Autonoma de Mexico (UNAM), Mexico

[*] Notice: The portion of the term of this patent subsequent to Apr. 21, 2009, has been disclaimed.

[21] Appl. No.: 303,141

[22] Filed: Sep. 8, 1994

Related U.S. Application Data

[63] Continuation of Ser. No. 115,250, Sep. 1, 1993, abandoned, which is a continuation of Ser. No. 987,063, Dec. 7, 1992, abandoned, which is a continuation of Ser. No. 853,867, Mar. 20, 1992, abandoned, which is a continuation of Ser. No. 628,528, Dec. 11, 1990, abandoned.

[30] Foreign Application Priority Data

Dec. 20, 1989 [MX] Mexico ..................................... 18801

[51] Int. Cl.$^6$ ........................ A61K 31/44; C07D 471/14
[52] U.S. Cl. ............................................. 514/292; 546/88
[58] Field of Search ................................ 546/88; 514/292

[56] References Cited

U.S. PATENT DOCUMENTS 3,282,649  11/1966  Bittner ..................................... 546/10
5,107,005  4/1992  Azuara ..................................... 556/116

OTHER PUBLICATIONS

Sone et al., J. Inorg. Nucl. Chem. (31), pp. 117–126, (1969).
Kwik, W. L., 2,9–Dimethyl–1,10–phenanthroline Copper Complexes with some sulfur–containing Amino Acids. Oct. 25, 1983. J. Chem. Soc. Dalton Trans. pp. 2269–2272.
Kwik, W. L. Complexes of (2,2'Bipyridyl) Copper(II) and (1,10–Phenanthroline)(Copper(II) with some Amino Acids. 1980. Org. nucl. chem. vol. 42, pp. 303–313.

*Primary Examiner*—Phyllis G. Spivack
*Attorney, Agent, or Firm*—Finnegan, Henderson, Farabow, Garrett & Dunner

[57] ABSTRACT

Copper amino acidate diimine nitrate compounds of the formula $[Cu(N-N)(N-O)]^{+}NO_3^-$, where (N—N) is a diimine selected from 1,10-phenanthroline or 4,7-dimethyl 1,10-phenanthroline and (N—O) is tyrosine-alaninate, threoninate, tryptophanate, valinate, isoleucinate, cysteinate, diglycinate, phenylalaninate, glycinate, histidinate, serinate, tryosinate, aspartate or alaninate and a process for preparing the compounds in which, while maintaining a pH between 5 and 7, a first aqueous solution of $Cu(NO_3)_2 \cdot 5H_2O$, having 30 to 35% by weight of elemental copper, is reacted with a second aqueous solution of the diimine having a ratio of 50 to 55% by weight diimine to solution to form a monodiimine nitrate as an intermediate reaction product having the formula $[Cu(N-N)(H_2O)_2]^+NO_3^-$ and then reacting the intermediate product with a third aqueous solution containing 10 to 15% by weight of an amino acid, while keeping an alkaline pH between 7 and 8, with an aqueous ammonical solution to obtain the copper compound.

11 Claims, No Drawings

COPPER AMINO ACIDATE DIIMINE NITRATE COMPOUNDS AND THEIR METHYL DERIVATIVES AND A PROCESS FOR PREPARING THEM

This application is a continuation, of application Ser. No. 08/115,250, filed Sep. 1, 1993, now abandoned, which is a continuation of application Ser. No. 08/115,250, filed Sep. 1, 1993, now abandoned, which is a continuation of application Ser. No. 07/987,063, filed Dec. 7, 1992, now abandoned, which is a continuation of application Ser. No. 07/853,867, filed Mar. 20, 1992, now abandoned, which is a continuation of application Ser. No. 07/628,628, filed Dec. 11, 1990, now abandoned.

BACKGROUND OF THE INVENTION

This invention relates to a process for obtaining new mixed copper amino acidate compounds from 1,10-phenanthrolines and their 4-7-dimethyl derivatives and the compounds obtained thereby to be used as anticancerigenic agents preferably in a therapeutic treatment of liquid and solid cancerigenic tumors such as leukemia. The compounds obtained are of the $^+NO_3^-$ type in which the (N—N) ligand corresponds to 1,10-phenanthroline or 4,7-dimethyl-1,10 phenanthroline and the (N—O) ligand corresponds to one of the amino acidates such as tyrosine-alaninate, treoninate, triptophanate, valinate, isoleucinate, cysteinate, diglycinate, phenylalaninate, glycinate, histidinate, serinate, tyrosinate, aspartate, and alaninate.

The process is characterized by the following steps: making an aqueous solution of an aliphatic alcohol and the phenanthroline and reacting the solution with a copper complex, preferably $Cu(NO_3)_2 \cdot 5H_2O$, at room temperature. Immediately after making the product, reacting it with an amino acidate in an aqueous solution while adjusting it to a slightly alkaline pH.

A type of drug for which a correlation between biological activity and structure has been found is the metal chelating agent such as iron, ruthenium, cobalt, manganese, zinc and copper (Dwyer, F. P. et al. *Nature*, 179 (1956), 425–426). Chelating agents can be designed to inactivate bacteria, viruses and fungi by capturing the metallic ions necessary for the metabolism of these microorganisms. They can also be supplied with metallic ions that prove toxic to them.

Studies related to the composition of physiological fluids have shown that the metallic ions present in these systems are largely found in the form of mixed complexes. Here the term mixed complex must be understood to mean all those coordination complexes with two or three chelate type ligands that are different one from the other, excluding the solvent of the chelate ligand category.

Sigel and colleagues (Sigel. H. et al., *JACS* 99:13 (1976), 4489–4496) have shown that in many cases the enzymatic action depends on an elementary process in which an enzyme-substrate complex is generated that presents characteristics analogous to those of a mixed complex.

Certain metallic chelates supplied in small concentrations are active against some bacteria, fungi, viruses and some tumorous cells.

It is well known, for instance, that *Staphylococcous pyrogenes*, which has been detected in infected wounds and has proved to be highly resistant to the action of many standard antibiotics, perishes in the presence of the iron and ruthenium (tetramethyl- 1,10phenanthroline)(acetylacetone)$^+$ complexes. The biological activity of these saturated chelate complexes is principally due to the stereochemistry of the complex as a whole, the ionic nature of the coordination sphere, the nature of the coordination center, the lyophilicity of the ligands, the redox potentials of the complexes, and the thermodynamic stability and kinetics of the metallic chelates.

Voloir and colleagues have studied the catalytic activity of the Co(II) and Cu(II) complexes with orthophenanthrolines in the oxidation processes of the NADH, $Q_4 H_2$ (quinone), $Q_9 H_2$ (ubiquinone) and cytochrome C substrates.

The [Cu(2,9-dimethyl-1.10-phenanthroline)$_2$]Cl$_2$ complex is an effective inhibitor of the growth of the plasmodium *Micoplasmacillisepticum*, a very dangerous pathogenic microorganism that induces pulmonary diseases in man. D. R. Williams has calculated the distribution percentages of the Cu(II). Fe(II). Mn(II) and Zn(II) ions with low weight ligands, the predominant molecules in human blood plasma: Cu(hys)(cys); (Cu(hys)$_2$; and Cu (hys)(cysh)$^+$ are among the most abundant complexes.

Mention is made in the literature of studies on the absorption of the Mn(gly)$_2$ and Mn(L-ala)$_2$ chelate complexes through the intestinal wall in dogs.

Kwik and colleagues have reported the synthesis of mixed complexes with the general formula [Cu(phenanthroline)(aminoacidate)X]$_n$H$_2$O, [Cu(bipyridine)(aminoacidate)X]$_n$H$_2$O), where x is Cl or ½ SO$_4$ and the amino acidate is glycinate, alaninate, valinate, tyrosinate, serinate, aspartate or glutamate.

Where the general synthesis method consists of preparing an aqueous solution with 5 mmol of $CuSO_4 5H_2O$ in 20 ml of distilled water which is slowly added to an ethanol solution, a solution blue in color is immediately formed. The mixture is magnetically shaken and at the same time a solution of 10 ml of HCl 0.1 M that contains one of the amino acidates is added, immediately followed by a solution of ammonium hydroxide 1 M until the solution becomes clear. The mixture that has been thus prepared is heated and shaken for 30 minutes; the heating process is continued until the volume is reduced by half. The product obtained is cooled in ice until a solid is formed, it is filtered, washed in small pieces in cold water and then in ethanol and is finally vacuum dried.

The applicant has developed a process to obtain new chelates by means of the synthesis and characterization of mixed chelate complexes of ions Mn(II), Fe(II), Ni(II), Co(II. III), Cu(II) Zn(II) and Ru(II) with ligands of the N—N(phenanthrolines and bipyridines and methyl substituted derivatives), O—O(acethylacetonate and salycilaldehydate ions) and N—O(amino acidate ions) type. These mixed chelate complexes have some type of potential biological activity.

With the ion Cu(II) and phenanthroline and their 4,7 dimethyl derivatives, complexes of the [CU(N—N)(N—O)] $^+NO_3^-$ type have been isolated.

SUMMARY OF THE INVENTION

A process for obtaining new mixed copper, amino acidate complexes from 1,10-phenanthrolines and their 4,7-dimethyl derivatives to be used as anticancerigenic agents is disclosed. These complexes have the formula [Cu(N—N)(N—O)]$^+NO_3^-$, in which the (N—N) ligand corresponds to the phenanthroline, preferably 4,7-dimethyl-1,10-phenanthroline, and the (N—O) ligand to an amino acidate such as tryosine-alaninate, treoninate, triptophanate, valinate, isoleucinate, cysteinate, diglycinate, phenylalaninate, glycinate, histidinate, serinate, tyrosinate, aspartate, and alaninate. The process comprises preparing an aqueous solution of a copper compound, preferably $CU(NO_3)_2.5H_2O$ having 30–35% by weight of elemental copper, preparing an aqueous-ethanolic solution with a diimine compound at a ratio of 50–55% diimine/solution; making the aqueous solutions react in a reactor at room temperature; stabilize the copper complex obtained (monodiimine nitrate) by maintaining a pH of between 5 and 7; adding to the complex obtained an aqueous solution of 10–15% by weight of an amino acid while keeping the reaction slightly alkaline at a pH of 7 to 8 to obtain a copper amino acidate diimine nitrate complex with anticancerigenic properties of the formula:

1) [Cu(1,10-phenanthroline)(tyrosine-alaninate)]$NO_3$;
2) [Cu(1,10-phenanthroline)(threoninate)]$NO_3$;
3) [Cu(1,10-phenanthroline)(tryptophanate)]$NO_3$;
4) [Cu(1,10-phenanthroline)(valinate)]$NO_3$;
5) [Cu(1,10-phenanthroline)(isoleucinate)]$NO_3$;
6) [Cu(1,10-phenanthroline)(cysteinate)]$NO_3$;
7) [Cu(1,10-phenanthroline)(diglycinate)]$NO_3$;
8) [Cu(1,10-phenanthroline)(phenylalinate)]$NO_3$;
9) [Cu(1,10-phenanthroline)(glycinate)]$NO_3$;
10) [Cu(1,10-phenanthroline)(histidinate)]$NO_3$;
11) [Cu(1,10-phenanthroline)(serininate)]$NO_3$;
12) [Cu(1,10-phenanthroline)(tyrosinate)]$NO_3$;
13) [Cu(1,10-phenanthroline)(aspartate)]$N_3$;
14) [Cu(1,10-phenanthroline)(alaninate)]$N_3$;
15) [Cu(4,7-dimethyl-1,10-phenanthroline)(phenylalaninate)]$NO_3$;
16) [Cu(4,7-dimethyl-1,10-phenanthroline)(glycinate)]$NO_3$;
17) [Cu(4,7-dimethyl-1,10-phenanthroline)(histidinate)]$NO_3$;
18) [Cu(4,7-dimethyl-1,10-phenanthroline)(tyrosinate)]$NO_3$;
19) [Cu(4,7-dimethyl-1,10-phenanthroline)(alaninate)]$NO_3$;

DETAILED DESCRIPTION OF THE INVENTION

The process for obtaining new mixed copper amino acidate compounds or complexes from 1,10 phenanthrolines and their 4,7 dimethyl derivatives to be used as anticancerigenic agents in which $Cu(NO_3)_2.5H_2O$ is used as raw material, makes it possible to obtain crystals that are highly soluble in water and furthermore the reactions that occur during the process of this invention take place at room temperature, thus avoiding any thermal decomposition that will affect therapeutic properties.

The process generally takes place in two stages according to the following:

1) To form the intermediary copper complex of the $[Cu(N—N)(H_2O)_2]^+NO_3^-$ type, an aqueous solution is prepared of a copper compound having 30–35% in weight of Cu and an aqueous-ethanolic solution of 50–55% in weight of the corresponding diimine. Both are immediately brought into contact in a reactor for approximately 5 minutes at room temperature. The resulting pH must be between 5 and 7.

2) To form the stabilized copper complex (monodiimine amino acidate nitrate), an aqueous solution is added to the above-mentioned intermediate product of 10–15% by weight of the amino acidate ion (N—O) while adjusting it to a slightly alkaline pH of 7-8 with an aqueous-ammoniacal solution.

The process is also characterized by passing the solution of the complex formed through a millipore filter in order to eliminate raw materials and secondary products, to sterilize the solution, and to obtain a pure product. It is concentrated by slight heating until the volume is reduced by half. When the mixture cools, the expected product precipitates and is finally filtered, thus giving a yield of 60%. To achieve greater purity, it is recrystalized in ethanol/water (to a ratio of 30/70). The crystals are royal blue in color.

The complexes formed as a result of this process are any of the following:

1) [Cu(1,10-phenanthroline)(tyrosine-alaninate)]$NO_3$;
2) [Cu(1,10-phenanthroline)(threoninate)]$NO_3$;
3) [Cu(1,10-phenanthroline)(tryptophanate)]$NO_3$;
4) [Cu(1,10-phenanthroline)(valinate)]$NO_3$;
5) [Cu(1,10-phenanthroline)(isoleucinate)]$NO_3$;
6) [Cu(1,10-phenanthroline)(cysteinate)]$NO_3$;
7) [Cu(1,10-phenanthroline)(diglycinate)]$NO_3$;
8) [Cu(1,10-phenanthroline)(phenylalinate)]$NO_3$;
9) [Cu(1,10-phenanthroline)(glycinate)]$NO_3$;
10) [Cu(1,10-phenanthroline)(histidinate)]$NO_3$;
11) [Cu(1,10-phenanthroline)(serininate)]$NO_3$;
12) [Cu(1,10-phenanthroline)(tyrosinate)]$NO_3$;
13) [Cu(1,10-phenanthroline)(aspartate)]$NO_3$;
14) [Cu(1,10-phenanthroline)(alaninate)]$NO_3$;
15) [Cu(4,7-dimethyl,1,10-phenanthroline)(phenylalaninate)]$NO_3$;
16) [Cu(4,7-dimethyl,1,10-phenanthroline)(glycinate)]$NO_3$;
17) [Cu(4,7-dimethyl,1,10-phenanthroline)(histidinate)]$NO_3$;
18) [Cu(4,7-dimethyl,1,10-phenanthroline)(tyrosinate)]$NO_3$;
19) [Cu(4,7-dimethyl,1,10-phenanthroline)(alaninate)]$NO_3$;

Examples of the invention are given below in order to illustrate it better, not with the purpose of restricting its scope.

EXAMPLE 1

To obtain a complex with the formula (Cu(1,10-phenanthroline) (tyrosine-alaninate)$NO_3$, a first aqueous-ethanolic solution was prepared in a container with 215.6 mg. of $Cu(NO_3)_2.5H_2O$; a second aqueous-ethanolic solution was immediately prepared with 180 mg of 1,10-phenanthroline; the aqueous solutions were then made to react in a reactor at room temperature, while keeping the pH between 5 and 7. An aqueous solution with 302.4 mg of tyrosine-alanine was subsequently added to the intermediary complex obtained and the reaction was kept at a pH of between 7 and 8 with an aqueous-ammoniacal solution for five minutes. The product obtained was immediately passed through a millipore filter; it was concentrated by slight heating and distilled in vacuum until the volume was reduced by half. Once cooled, the mixture of the aromatic complex obtained from copper tyrosine-alaninate was precipitated. It was then filtered and recrystalized in an ethanol/water mixture (with a ratio of 30/70).

The crystals obtained were royal blue in color and their characterization was the following:

COMPOUND FORMULA: [Cu(1,10-phenanthroline)(tyrosine-alaninate)]NO$_3$

ELEMENT ANALYSIS OBTAINED (%): 51.82 C: 4.30 H: 10.12 N

CALCULATED ELEMENT ANALYSIS (%): (51.74) C: (4.13) H: (10.06) N

BORH MAGNETONS (^m. eff): 1.83

CONDUCTIVITY (Ohms.mol.cm$^{-1}$): 225 (water)

max visible (nm): 626

IR (cm$^{-1}$): 1609, 1380, 1107, 873, 846 and 827, 775, 721 (IR=Infrared analysis).

EXAMPLE 2

A complex with the formula [Cu(1,10-phenanthroline)(threoninate)]NO$_3$ was obtained by preparing an aqueous-ethanolic solution in a container with 215.6 mg. (1 mmol) of Cu(NO$_3$)$_2$.5H$_2$O and also preparing an aqueous-ethanolic solution with 180 mg (1 mmol) of 1,10-phenanthroline. These aqueous solutions were then made to react in a reactor at room temperature; shortly afterwards, while keeping the pH between 5 and 7, an aqueous solution of 141.6 mg of threonine was added to the intermediary complex obtained of the formula [Cu(1,10-phenanthroline)]NO$_3$. The reaction was kept at a pH of between 7 and 8 with an aqueous-ammoniacal solution for 5 minutes. The product obtained was immediately passed through a millipore filter. It was concentrated by slight heating and distilled in vacuum until the volume was reduced by half. When the mixture had cooled, the aromatic complex based on copper threoninate was precipitated. It was then filtered and recrystalized in an ethanol/water mixture (at a ratio of 30/70). The crystals obtained were royal blue in color and their characterization was the following:

COMPOUND FORMULA: [Cu(1,10-phenanthroline)(threoninate)]NO$_3$

ELEMENT ANALYSIS OBTAINED (%): 45.70 C: 3.9 H: 13.4 N

CALCULATED ELEMENT ANALYSIS (%): (45.34) C: (3.81) H: (13.22) N

BORH MAGNETONS (μ. eff): 1.75

CONDUCTIVITY (Ohms.mol.cm$^{-1}$): 85 (water)

λ max visible (nm): 611

IR (cm$^{-1}$): 1523, 1380, 1160, 1055, 850, 790, 723, 646.

EXAMPLE 3

A complex with the formula [Cu(1,10-phenanthroline)(tryptophanate)]NO$_3$ was obtained following the technique described in Examples 1 and 2 to obtain the intermediary complex with the formula [Cu(1,10-phenanthroline)]NO$_3$. While keeping the pH between 5 and 7, an aqueous solution was then added with 226.8 mg of tryptophane; the reaction was kept at a pH of between 7 and 8 with an aqueous-ammoniacal solution for 5 minutes. The product obtained was immediately passed through a millipore filter. It was concentrated with slight heating and distilled in vacuum until the volume was reduced by half. When the mixture had cooled, the aromatic complex based on copper tryptophanate was precipitated. It was filtered and recrystalized in an ethanol/water mixture (at a ratio of 30/70). The crystals obtained were royal blue in color and their characterization was the following:

COMPOUND FORMULA: [Cu(1,10-phenanthroline)(tryptophanate)]NO$_3$

ELEMENT ANALYSIS OBTAINED (%): 51.0 C: 3.8 H: 13.5 N

CALCULATED ELEMENT ANALYSIS (%): (50.28) C: (3.76) H: (13.76) N

BORH MAGNETONS (μ. eff): 1.85

CONDUCTIVITY (Ohms.mol.cm$^{-1}$): 135 (water)

λ max visible (nm): 615

IR (cm$^{-1}$): 1611, 1521, 1380, 1141, 873, 841, 742 and 719.

EXAMPLE 4

A complex with the formula [Cu(1,10-phenanthroline)(valinate)]NO$_3$ was obtained following the technique described in Examples 1 and 2 to obtain the intermediary complex with the formula [Cu(1,10-phenanthroline)]NO$_3$. While keeping the pH at between 5 and 7, an aqueous solution was then added with 139.2 mg of valine; the reaction was regulated with a pH of between 7 and 8 with an aqueous-ammoniacal solution for 5 minutes. The product obtained was immediately passed through a millipore filter. It was concentrated by slight heating and distilled in vacuum until the volume was reduced by half. When the mixture cooled, the aromatic complex based on copper valinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(valinate)]NO$_3$

ELEMENT ANALYSIS OBTAINED (%): 48.6 C: 4.5 H: 13.4 N

CALCULATED ELEMENT ANALYSIS (%): (48.40) C: (4.30) H: (13.28) N

BORH MAGNETONS (μ. eff): 1.79

CONDUCTIVITY (Ohms.mol.cm$^{-1}$): 118 (water)

λ max visible (nm): 654

IR (cm$^{-1}$): 1655, 1522, 1380; 1195, 1050, 832, 765, 723, 652.

EXAMPLE 5

A complex with the formula [Cu(1,10-phenanthroline)(i-soleucinate)]NO$_3$ was obtained; the intermediary complex was prepared with the formula [Cu(1,10-phenanthroline)]NO$_3$ by means of the technique described in Examples 1 and 2 and its pH was kept at between 5 and 7; an aqueous solution was then added with 156 mg of isoleucine; the reaction was regulated with a pH of between 7 and 8 with an aqueous-ammoniacal solution for 5 minutes. It was immediately passed through a millipore filter. It was concentrated by slight heating and distilled in vacuum until the volume had reduced by half. When the mixture cooled, the aromatic complex based on copper isoleucinate precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(i-soleucininate)]NO$_3$

ELEMENT ANALYSIS OBTAINED (%): 49.4 C: 4.7 H: 12.9 N

CALCULATED ELEMENT ANALYSIS (%): (49.60) C: (4.62) H: (12.85) N

BORH MAGNETONS (μ. eff): 1.83

CONDUCTIVITY (Ohms.mol.cm$^{-1}$): 28.5 (ethanol)

λ max visible (nm): 610

IR (cm$^{-1}$): 1650, 1580, 1525; 1380, 1110, 875, 854, 825, 780, 450, 580, 430.

EXAMPLE 6

A complex with the formula [Cu(1,10-phenanthroline)(cysteinate)]NO$_3$ was obtained, the intermediary complex was prepared with the formula [Cu(1,10-phenanthroline)]NO$_3$ following the technique described in Examples 1 and 2 and its pH was kept at between 5 and 7; an aqueous solution with 145.9 mg of cysteine was then added and the reaction regulated with a pH of between 7 and 8 with an aqueous-ammoniacal solution for 5 minutes. The product obtained was immediately passed through a millipore filter. It was concentrated by means of slight heating and distilled in vacuum until the volume had been reduced by half. When the mixture cooled, the aromatic complex based on copper cysteinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(cysteinate)]NO$_3$

ELEMENT ANALYSIS OBTAINED (%): 42.35 C: 3.34 H: 13.14 N

CALCULATED ELEMENT ANALYSIS (%): (42.3) C: (3.31) H: (13.15) N

BORH MAGNETONS (μ. eff): 1.82

CONDUCTIVITY (Ohms.mol.cm$^{-1}$): 61 (nitrobenzene)

λ max visible (nm): 423

IR (cm$^{-1}$): 1645, 1380, 1135, 1105, 1005, 835, 757, 669, 642, 570.

EXAMPLE 7

A complex with the formula [Cu(1,10-phenanthroline)(diglycinate)]NO$_3$ was obtained; the intermediary complex was prepared with the formula [Cu(1,10-phenanthroline)]NO$_3$ following the technique described in Examples 1 and 2; its pH was kept at between 5 and 7; an aqueous solution with 158.4 mg of diglycine was subsequently added, and the reaction was regulated at a pH of between 7 and 8 with an aqueous-ammoniacal solution for 5 minutes. The product obtained was immediately passed through a millipore filter. It was concentrated by means of slight heating and distilled in vacuum until half the volume remained. When the mixture cooled, the aromatic complex based on copper diglycinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(diglycinate)]NO$_3$

ELEMENT ANALYSIS OBTAINED (%): 43.5 C: 3.6 H: 12.92 N

CALCULATED ELEMENT ANALYSIS (%): (43.92) C: (3.43) H: (12.82) N

BORH MAGNETONS (μ. eff): 1.79

CONDUCTIVITY (Ohms.mol.cm$^{-1}$): 100 (water)

λ max visible (nm): 615

IR (cm$^{-1}$): 1628, 1520, 1380, 1172, 1107, 852, 723, 650, 430.

EXAMPLE 8

A complex with the formula [Cu(1,10-phenanthroline)(phenylalinate)]NO$_3$ was obtained; the intermediary complex was prepared with the formula [Cu(1,10-phenanthroline)]NO$_3$ by means of the technique described in Examples 1 and 2. Keeping its pH at between 5 and 7; an aqueous solution with 104.4 mg of phenylalanine was subsequently added, the reaction was regulated at a pH of between 7 and 8 with an aqueous-ammoniacal solution for 5 minutes. The product obtained was immediately passed through a millipore filter. It was concentrated by means of slight heating and distilled in vacuum until half the volume remained. When the mixture cooled, the aromatic complex based on copper phenylalaninate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(phenylalaninate)]NO$_3$

ELEMENT ANALYSIS OBTAINED (%): 51.43 C: 4.44 H: 11.34 N

CALCULATED ELEMENT ANALYSIS (%): (51.69) C: (4.10) H: (11.48) N

BORH MAGNETONS (μ. eff): 1.76

CONDUCTIVITY (Ohms.mol.cm$^{-1}$): 123 (water)

λ max visible (nm): 610

IR (cm$^{-1}$): 1585, 1520, 1380; 1108, 855, 830, 769, 740, 670, 650, 639, 555, 440.

EXAMPLE 9

A complex with the formula [Cu(1,10-phenanthroline)(glycinate)]NO$_3$ was obtained; the intermediary complex was prepared with the formula [Cu(1,10-phenanthroline)]NO$_3$ following the technique described in Examples 1 and 2, and its pH was kept at between 5 and 7; an aqueous solution with 89 mg of glycine was subsequently added, and the reaction was regulated at a pH of between 7 and 8 with an aqueous-ammoniacal solution for 5 minutes. The product obtained was immediately passed through a millipore filter. It was concentrated by means of slight heating and distilled in vacuum until half the volume remained. When the mixture cooled, the aromatic complex based on copper glycinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(glycinate)]NO$_3$

ELEMENT ANALYSIS OBTAINED (%): 44.25 C: 3.12 H: 14.26 N

CALCULATED ELEMENT ANALYSIS (%): (44.27) C: (3.16) H: (14.75) N

BORH MAGNETONS (μ. eff): 1.85

CONDUCTIVITY (Ohms.mol.cm$^{-1}$): 126 (water)

λ max visible (nm): 615

IR (cm$^{-1}$): 1580, 1520, 1380; 1225 and 1105, 1050, 855, 780, 725, 665, 650, 440.

EXAMPLE 10

A complex with the formula [Cu(1,10-phenanthroline)(histidinate)]NO$_3$ was obtained; the intermediary complex was prepared with the formula [Cu(1,10-phenanthroline)]NO$_3$ following the technique described in Examples 1 and 2, keeping its pH at between 5 and 7; an aqueous solution with 176.4 mg of histidine was subsequently added and the reaction was regulated at a pH of between 7 and 8 with an aqueous-ammoniacal solution for 5 minutes. The product obtained was immediately passed through a millipore filter. It was concentrated by means of slight heating and distilling in vacuum until half the volume remained. When the mixture cooled, the aromatic complex based on copper histidinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(histidinate)]NO$_3$

ELEMENT ANALYSIS OBTAINED (%): 49.0 C: 3.56 H: 15.65 N

CALCULATED ELEMENT ANALYSIS (%): (48.8) C: (13.59) H: (15.65) N

BORH MAGNETONS (μ. eff): 1.65

CONDUCTIVITY (Ohms.mol.cm$^{-1}$): 213 (water)

λ max visible (nm): 665

IR (cm$^{-1}$): 1590, 1525, 1380; 1149, 1110, 855, 838, 780, 725, 675, 653, 565, 440.

EXAMPLE 11

A complex with the formula [Cu(1,10-phenanthroline)(serinate)]NO$_3$ was obtained; the intermediary complex was prepared with the formula [Cu(1,10-phenanthroline)]NO$_3$ following the technique described in Examples 1 and 2. Keeping its pH at between 5 and 7, an aqueous solution with 124.8 mg of serine was subsequently added and the reaction was regulated at a pH of between 7 and 8 with an aqueous-ammoniacal solution for 5 minutes. The product obtained was immediately passed through a millipore filter. It was concentrated by means of slight heating and distilled in vacuum until half the volume remained. When the mixture cooled, the aromatic complex based on copper serinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(serinate)]NO$_3$

ELEMENT ANALYSIS OBTAINED (%): 44.11 C: 3.30 H: 13.68 N

CALCULATED ELEMENT ANALYSIS (%): (44.07) C: (3.20) H: (13.70) N

BORH MAGNETONS (μ. eff): 1.78

CONDUCTIVITY (Ohms.mol.cm$^{-1}$): 90 (water)

λ max visible (nm): 612

IR (cm$^{-1}$): 1521, 1380; 1170, 860, 829, 723, 653.

EXAMPLE 12

A complex with the formula [Cu(1,10-phenanthroline)(tyrosinate)]NO$_3$ was obtained; the intermediary complex was prepared with the formula [Cu(1,10-phenanthroline)]NO$_3$ following the technique described in Examples 1 and 2. Keeping its pH at between 5 and 7, an aqueous solution with 216.0 mg of tyrosine was subsequently added and the reaction was regulated at a pH of between 7 and 8 with an aqueous-ammoniacal solution for 5 minutes. The product obtained was immediately passed through a millipore filter. It was concentrated by slight heating and distillation in vacuum until half the volume remained. When the mixture cooled, the aromatic complex based on copper tyrosinate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(tyrosinate)]NO$_3$

ELEMENT ANALYSIS OBTAINED (%): 49.32 C: 3.60 H: 12.35 N

CALCULATED ELEMENT ANALYSIS (%): (49.40) C: (3.90) H: (12.13) N

BORH MAGNETONS (μ. eff): 1.91

CONDUCTIVITY (Ohms.mol.cm$^{-1}$): 136 (water)

λ max visible (nm): 610

IR (cm$^{-1}$): 1590, 1520; 1380, 1180 1110, 915, 880, 850, 815, 780, 745, 650, 550, 440.

EXAMPLE 13

A complex with the formula [Cu(1,10-phenanthroline)(aspartate)]NO$_3$ was obtained; the intermediary complex was prepared with the formula [Cu(1,10-phenanthroline)]NO$_3$ following the technique described in Examples 1 and 2. Keeping its pH at between 5 and 7, an aqueous solution with 158.4 mg of aspartic acid was subsequently added and the reaction was regulated at a pH of between 7 and 8 with an aqueous-ammoniacal solution for 5 minutes. The product obtained was immediately passed through a millipore filter. It was concentrated by slight heating and distillation in vacuum until the volume was reduced by half. When the mixture cooled, the aromatic complex based on copper aspartate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(aspartate)]NO$_3$

ELEMENT ANALYSIS OBTAINED (%): 43.8 C: 3.31 H: 12.79 N

CALCULATED ELEMENT ANALYSIS (%): (43.91) C: (3.22) H: (12.80) N

BORH MAGNETONS (μ. eff): 1.85

CONDUCTIVITY (Ohms.mol.cm$^{-1}$): 104.5 (methanol)

λ max visible (nm): 628

IR (cm$^{-1}$): 1609, 1518, 1380, 1143, 1105, 854 and 827, 723, 644.

EXAMPLE 14

A complex with the formula [Cu(1,10-phenanthroline)(alaninate)]NO$_3$ was obtained; the intermediary complex was prepared with the formula [Cu(1,10-phenanthroline)]NO$_3$ following the technique described in Examples 1 and 2. Keeping its pH at between 5 and 7, an aqueous solution with 105.6 mg of alanine was subsequently added and the reaction was regulated at a pH of between 7 and 8 with an aqueous-ammoniacal solution for 5 minutes. The product obtained was immediately passed through a millipore filter. It was concentrated by slight heating and distillation in vacuum until the volume was reduced by half. When the mixture cooled, the aromatic complex based on copper alaninate was precipitated. It was filtered and recrystalized in an ethanol/water mixture (at a ratio of 30/70).

The crystals obtained were royal blue in color and their characterization was the following:

COMPOUND FORMULA: [Cu(1,10-phenanthroline)(alaninate)]$NO_3$

ELEMENT ANALYSIS OBTAINED (%): 42.96 C: 3.40 H: 13.50 N

CALCULATED ELEMENT ANALYSIS (%): (43.74) C: (3.88) H: (13.60) N

BORH MAGNETONS (μ. eff): 1.95

CONDUCTIVITY (Ohms.mol.$cm^{-1}$): 119 (water)

λ max visible (nm): 609

IR ($cm^{-1}$): 1590, 1520, 1380, 1150 and 1115, 930, 875, 855, 780, 725, 650, 439.

EXAMPLE 15

In order to obtain a complex with the formula [Cu(4,7-dimethyl-1,10phenanthroline)(phenylalaninate)]$NO_3$, an aqueousethanolic solution with 215.6 mg Cu$(NO_3)_2$.5$H_2O$ was prepared in a container; a second aqueous-ethanolic solution with 208 mg of 4,7-dimethyl-1,10phenanthroline was immediately prepared; the aqueous solutions were then made to react in a reactor at room temperature. Soon after, while keeping the pH at between 5 and 7, an aqueous solution with 104.4 mg of phenylalanine was subsequently added to the intermediary complex obtained. The reaction was kept at a pH of between 7 and 8 and was regulated with an aqueous-ammoniacal solution for 5 minutes. The product obtained was immediately passed through a millipore filter. It was concentrated by slight heating and distillation in vacuum until the volume was reduced by half. Once the mixture had been cooled, the aromatic complex based on copper phenylalaninate was precipitated. It was filtered and recrystalized in a mixture of ethanol/water (at a ratio of 30/70).

The crystals obtained were royal blue in color and their characterization was the following:

COMPOUND FORMULA: [Cu(4,7-dimethyl-1,10-phenanthroline)(phenylalaninate)]$NO_3$

ELEMENT ANALYSIS OBTAINED (%): 55.50 C: 4.30 H: 11.30 N

CALCULATED ELEMENT ANALYSIS (%): (55.47) C: (4.21) H: (11.25) N

BORH MAGNETONS (μ. eff): 2.07

CONDUCTIVITY (Ohms.mol.$cm^{-1}$): 125 (water)

λ max visible (nm): 609

IR ($cm^{-1}$): 1580, 1525, 1380, 1230, 1170, 1025, 865 and 855, 749 and 720, 700, 665, 645, 570, 430.

EXAMPLE 16

To obtain a complex with the formula [Cu(4,7-dimethyl-1,10phenanthroline)(glycinate)]$NO_3$, an aqueous-ethanolic solution with 215.6 mg of Cu$(NO_3)_2$.5$H_2O$ was prepared in a vessel; a second aqueous-ethanolic solution with 208 mg of 4,7-dimethyl-1,10-phenanthroline was immediately prepared; the aqueous solutions were then made to react in a reactor at room temperature. Soon after, while keeping the pH at between 5 and 7, an aqueous solution with 89 mg of glycinate was subsequently added to the intermediary complex obtained. The reaction was kept at a pH of between 7 and 8 and was regulated with an aqueous-ammoniacal solution for 5 minutes. The product obtained was immediately passed through a millipore filter. It was concentrated by slight heating and distillation in vacuum until the volume was reduced by half. Once the mixture had been cooled, the intermediary complex obtained from copper glycinate was precipitated. It was then filtered and recrystalized in an ethanol/water mixture (at a ratio of 30/70).

The crystals obtained were royal blue in color and their characterization was the following:

COMPOUND FORMULA: [Cu(4,7-dimethyl-1,10-phenanthroline)(glycinate)]$NO_3$

ELEMENT ANALYSIS OBTAINED (%): 47.20 C: 4.0 H: 13.74 N

CALCULATED ELEMENT ANALYSIS (%): (47.12) C: (3.93) H: (13.74) N

BORH MAGNETONS (μ. eff): 1.72

CONDUCTIVITY (Ohms.mol.$cm^{-1}$): 112 (water)

λ max visible (nm): 603.7

STRUCTURE (R): 0.046

IR ($cm^{-1}$): 1579, 1525, 1380, 1170, 1120, 1030, 870, 725, 690, 665, 645, 430.

EXAMPLE 17

To obtain a complex with the formula [Cu(4,7-dimethyl-1,10phenanthroline)(histidinate)]$NO_3$, an aqueous-ethanolic solution with 215.6 mg of Cu$(NO_3)_2$.5$H_2O$ was prepared in a vessel; a second aqueous-ethanolic solution with 208 mg of 4,7-dimethyl-1,10-phenanthroline was immediately prepared; the aqueous solutions were then made to react in a reactor at room temperature. Soon after, while keeping the pH at between 5 and 7, an aqueous solution with 176.4 mg of histidine was subsequently added to the intermediary complex obtained. The reaction was kept at a pH of between 7 and 8 and was regulated with an aqueous-ammoniacal solution for 5 minutes. The product obtained was immediately passed through a millipore filter. It was concentrated by slight heating and distillation in vacuum until the volume was reduced by half. Once the mixture had cooled, the aromatic complex obtained from copper histidinate was precipitated. It was then filtered and recrystalized in an ethanol/water mixture (with a ratio of 30/70).

The crystals obtained were royal blue in color and their characterization was the following:

COMPOUND FORMULA: [Cu(4,7-dimethyl-1,10-phenanthroline)(histidinate)]$NO_3$

ELEMENT ANALYSIS OBTAINED (%): 49.10 C: 4.2 H: 17.3 N

CALCULATED ELEMENT ANALYSIS (%): (49.22) C: (4.10) H: (17.23) N

BORH MAGNETONS (μ. eff): 1.62

CONDUCTIVITY (Ohms.mol.$cm^{-1}$): 205 (water)

λ max visible (nm): 666.5

IR ($cm^{-1}$): 1640, 1485, 1455, 1380, 1255, 1160, 1005, 1039, 840, 780, 655, 560, 430.

EXAMPLE 18

In order to obtain a complex with the formula [Cu(4,7-dimethyl-1,10phenanthroline)(tyrosinate)]$NO_3$, an aqueousethanolic solution with 215.6 mg of Cu$(NO_3)_2$.5$H_2O$ was prepared in a vessel; a second aqueous-ethanolic solution with 208 mg of 4,7-dimethyl-1,10-phenanthroline was immediately prepared; the aqueous solutions were then made to react in a reactor at room temperature. Soon after, while keeping the pH at between 5 and 7, an aqueous solution with 216 mg of tyrosine was subsequently added to the intermediary complex obtained. The reaction was kept at a pH of between 7 and 8 and was regulated with an aqueous-ammoniacal solution for 5 minutes. The product obtained was immediately passed through a millipore filter. It was concentrated by slight heating and distillation in vacuum until the volume had been reduced by half. Once the mixture had cooled, the aromatic complex obtained from copper tyrosinate was precipitated. It was then filtered and recrystalized in an ethanol/water mixture (at a ratio of 30/70).

The crystals obtained were royal blue in color and their characterization was the following:

COMPOUND FORMULA: [Cu(4,7-dimethyl-1,10-phenanthroline)(tyrosinate)]NO$_3$

ELEMENT ANALYSIS OBTAINED (%): 53.81 C: 4.31 H: 10.89 N

CALCULATED ELEMENT ANALYSIS (%): (53.74) C: (4.28) H: (10.90) N

BORH MAGNETONS ($\mu$. eff): 1.96

CONDUCTIVITY (Ohms.mol.cm$^{-1}$): 125 (water)

$\lambda$ max visible (nm): 613.9

IR (cm$^{-1}$): 1615, 1580, 1525, 1380, 1175, 1120, 980, 935, 870, 850 and 815, 725, 690, 650, 540.

EXAMPLE 19

In order to obtain a complex with the formula [Cu(4,7-dimethyl-1,10phenanthroline)(alaninate)]NO$_3$, an aqueous-ethanolic solution with 215.6 mg of Cu(NO$_3$)$_2$.5H$_2$O was prepared in a vessel; a second aqueous-ethanolic solution with 208 mg of 4,7-dimethyl-1,10-phenanthroline was immediately prepared; the aqueous solutions were then made to react in a reactor at room temperature. Soon after, while keeping the pH at between 5 and 7, an aqueous solution with 105.6 mg of alaninate was subsequently added to the intermediary complex obtained. The reaction was kept at a pH of between 7 and 8 and was regulated with an aqueous-ammoniacal solution for 5 minutes. The product obtained was immediately passed through a millipore filter. It was concentrated by slight heating and distillation in vacuum until the volume had been reduced by half. Once the mixture had cooled, the aromatic complex obtained from copper alaninate was precipitated. It was then filtered and recrystalized in an ethanol/water mixture (at a ratio of 30/70).

The crystals obtained were royal blue in color and were characterized as follows:

COMPOUND FORMULA: [Cu(4,7-dimethyl-1,10-phenanthroline)(alaninate)]NO$_3$

ELEMENT ANALYSIS OBTAINED (%): 55.5 C: 4.3 H: 11.3 N

CALCULATED ELEMENT ANALYSIS (%): (55.47) C: (4.21) H: (11.25) N

BORH MAGNETONS ($\mu$. eff): 1.89

CONDUCTIVITY (Ohms.mol.cm$^{-1}$): 117 (water)

$\lambda$ max visible (nm): 601.5

IR (cm$^{-1}$): 1610, 1555, 1380, 1161, 1110, 1065, 920, 850, 740 and 730, 695, 605,430.

What is claim is:

1. A process for preparing a copper amino acidate diimine nitrate compound of the formula [CU(N—N)(N—O)]$^+$ NO$_3^-$, where the (N—N) ligand is a diimine selected from the group consisting of 1,10-phenanthroline and 4,7-dimethyl-1,10-phenanthroline and the (N—O) ligand is an amino acidate selected from the group consisting of tyrosine-alaninate, threoninate, tryptophanate, valinate, isoleucinate, cysteinate, diglycinate, phenylalaninate, glycinate, histidiante, serinate, tryosinate, aspartate, and alaninate; consisting essentially of the steps of reacting at room temperature in a reactor and while maintaining a pH of between 5 and 7, a first aqueous solution of Cu(NO$_3$)$_2$.5H$_2$O, having 30 to 35% by weight of elemental copper, with a second aqueous solution of said diimine having a ratio of 50 to 55% by weight diimine to solution to form a monodiimine nitrate as an intermediate reaction product having the formula [Cu(N—N)(H$_2$O)$_2$]$^+$NO$_3^-$ and then reacting said reaction product with a third aqueous solution containing 10 to 15% by weight of an amino acid selected from the group consisting of tyrosine-alanine, threonine, tryptophan, valine, isoleucine, cysteine, diglycine, phenylalanine, glycine, histidine, serine, tryosine, aspartic acid, and alanine, while keeping an alkaline pH between 7 and 8 with an aqueous-ammonical solution, to obtain a solution of a copper amino acidate diimine nitrate compound selected from the group consisting of:

[Cu(1,10-phenanthroline)(tyrosine-alaninate)]NO$_3$;

[Cu(1,10-phenanthroline)(threoninate)]NO$_3$;

[Cu(1,10-phenanthroline)(tryptophanate)]NO$_3$;

[Cu(1,10-phenanthroline)(valinate)]NO$_3$;

[Cu(1,10-phenanthroline)(isoleucinate)]NO$_3$;

[Cu(1,10-phenanthroline)(cysteinate)]NO$_3$;

[Cu(1,10-phenanthroline)(diglycinate)]NO$_3$;

[Cu(1,10-phenanthroline)(phenylalinate)]NO$_3$;

[Cu(1,10-phenanthroline)(glycinate)]NO$_3$;

[Cu(1,10-phenanthroline)(histidinate)]NO$_3$;

[Cu(1,10-phenanthroline)(serininate)]NO$_3$;

[Cu(1,10-phenanthroline)(tyrosinate)]NO$_3$;

[Cu(1,10-phenanthroline)(aspartate)]NO$_3$;

[Cu(1,10-phenanthroline)(alaninate)]NO$_3$;

[Cu(4,7-dimethyl,1,10-phenanthroline)(phenylalaninate)] NO$_3$;

[Cu(4,7-dimethyl,1,10-phenanthroline)(glycinate)]NO$_3$;

[Cu(4,7-dimethyl,1,10-phenanthroline)(histidinate)]NO$_3$;

[Cu(4,7-dimethyl,1,10-phenanthroline)(tyrosinate)]NO$_3$;

[Cu(4,7-dimethyl,1,10-phenanthroline)(alaninate)]NO$_3$;

and then separating the compound from the solution.

2. The process of claim 1, wherein the reaction between the first and second aqueous solutions is carried out for about 5 minutes.

3. The process of claim 2, wherein the third aqueous solution contains from 12 to 15% by weight of the amino acid.

4. The process of claim 1, wherein the solution of the compound is passed through a millipore filter, slightly heated, distilled in a vacuum and sterilized.

5. A copper amino acidate diimine nitrate compound selected from the group consisting of:

[Cu(1,10-phenanthroline)(tyrosine-alaninate)]NO$_3$;

[Cu(1,10-phenanthroline)(threoninate)]NO$_3$;

[Cu(1,10-phenanthroline)(tryptophanate)]NO$_3$;

[Cu(1,10-phenanthroline)(valinate)]NO$_3$;

[Cu(1,10-phenanthroline)(isoleucinate)]NO$_3$;
[Cu(1,10-phenanthroline)(cysteinate)]NO$_3$;
[Cu(1,10-phenanthroline)(diglycinate)]NO$_3$;
[Cu(1,10-phenanthroline)(phenylalinate)]NO$_3$;
[Cu(1,10-phenanthroline)(histidinate)]NO$_3$;
[Cu(1,10-phenanthroline)(serininate)]NO$_3$;
[Cu(1,10-phenanthroline)(tyrosinate)]NO$_3$;
[Cu(1,10-phenanthroline)(aspartate)]NO$_3$;
[Cu(1,10-phenanthroline)(alaninate)]NO$_3$;
[Cu(4,7-dimethyl,1,10-phenanthroline)(phenylalaninate)]NO$_3$;
[Cu(4,7-dimethyl,1,10-phenanthroline)(glycinate)]NO$_3$;
[Cu(4,7-dimethyl,1,10-phenanthroline)(histidinate)]NO$_3$;
[Cu(4,7-dimethyl,1,10-phenanthroline)(tyrosinate)]NO$_3$; and
[Cu(4,7-dimethyl,1,10-phenanthroline)(alaninate)]NO$_3$.

6. [Cu(4,7-dimethyl,1,10-phenanthroline)(phenylalaninate)]NO$_3$.

7. [Cu(4,7-dimethyl,1,10-phenanthroline)(glycinate)]NO$_3$.

8. [Cu(4,7-dimethyl,1,10-phenanthroline)(histidinate)]NO$_3$.

9. [Cu(4,7-dimethyl,1,10-phenanthroline)(alaninate)]NO$_3$.

10. [Cu(4,7-dimethyl,1,10-phenanthroline)(tyrosinate)]NO$_3$.

11. A pharmaceutical composition for the treatment of liquid and solid cancerigenic tumors comprising an effective amount of at least one copper amino acidate diimine nitrate compound of claim 5 and a pharmaceutically acceptable carrier.

* * * * *

UNITED STATES PATENT AND TRADEMARK OFFICE
CERTIFICATE OF CORRECTION

PATENT NO. : 5,576,326
DATED : November 19, 1996
INVENTOR(S) : Lena R. Azuara

It is certified that error appears in the above-indentified patent and that said Letters Patent is hereby corrected as shown below:

Claim 1, column 14, line 36, change "phenylalinate" to --phenylalaninate--.

Claim 5, column 15, line 4, change "phenylalinate" to --phenylalaninate--.

Signed and Sealed this

Twentieth Day of May, 1997

Attest:

BRUCE LEHMAN

*Attesting Officer*  *Commissioner of Patents and Trademarks*